United States Patent [19]
Giles, Jr.

[11] Patent Number: 6,025,363
[45] Date of Patent: *Feb. 15, 2000

[54] COMPOSITION FOR SUPPRESSING APPETITE

[76] Inventor: James A. Giles, Jr., 2030 - 29th St., San Diego, Calif. 92104

[ * ] Notice: This patent is subject to a terminal disclaimer.

[21] Appl. No.: 09/289,197

[22] Filed: Apr. 9, 1999

Related U.S. Application Data

[63] Continuation of application No. 09/193,939, Nov. 17, 1998.

[51] Int. Cl.⁷ ............................ A61K 31/52; A61K 31/35

[52] U.S. Cl. ............................................ 514/263; 514/460

[58] Field of Search ...................................... 514/460, 263

[56] References Cited

U.S. PATENT DOCUMENTS

| | | | |
|---|---|---|---|
| 5,273,754 | 12/1993 | Mann | 424/440 |
| 5,770,207 | 6/1998 | Bewicke | 424/195.1 |
| 5,798,101 | 8/1998 | Haveson | 424/195.1 |

*Primary Examiner*—Raymond Henley, III
*Attorney, Agent, or Firm*—Baker & Maxham; Peter R. Martinez

[57] ABSTRACT

A method for promoting appetite suppression without promoting anxiety, by administering at least one kavalactone and at least one methylxanthine. The compositions balance the energizing effects of methylxanthine stimulants with the calming effects of kavalactone relaxants. The compositions of the invention are presented in a variety of formulations, with or without other active ingredients such as vitamins and minerals.

27 Claims, No Drawings

US 6,025,363

COMPOSITION FOR SUPPRESSING APPETITE

REFERENCED TO RELATED APPLICATION

This is a continuation of application Ser. No. 09/193,939 filed November 17, 1998, titled COMPOSITION FOR ACHIEVING AN ALERT, YET CALM STATE.

BACKGROUND OF THE INVENTION

1. Field of the Invention

The present invention relates generally to dietary supplements, and more particularly, to a composition comprising kava and caffeine that produces an alert, yet calm state in a host subject. Additionally, the composition suppresses appetite in host subjects.

2. Discussion of the Related Art

Throughout history, humans have consumed a wide variety of substances to affect their mental or physical state. Our modern non-stop society places ever increasing demands on our time, and many people consume stimulants to keep them wakefull and attentive for extended periods. These stimulants can cause overstimulation, so many people use relaxants of various types. Unfortunately, the relaxants and stimulants do not act synergistically, and the individual swings from an over-stimulated condition to an over-sedated condition.

The most widespread stimulant is caffeine, which is primarily ingested by drinking tea or coffee. Caffeine affects the central nervous system, mainly the cerebrum. Caffeine is found in coffee beans, tea, cola nuts, guarana, cacao seeds, and mate. Caffeine can also be manufactured synthetically.

The chemical name for caffeine is 1,3,7-trimethylxanthine. Other common methylxanthine stimulants include 1,3-dimethylxanthine (found in tea and commonly called theophylline), and 3,7-dimethylxanthine (found in cacao seeds and tea, and commonly called theobromine).

Products containing caffeine are ubiquitous. A sampling of such products includes coffees, teas, soft drinks, chocolate products, cold-relief products, diet aids, various foods including puddings and, of course, products specifically designed to keep people awake and alert.

Although caffeine is employed in countless products, it can have undesirable side effects. The most common side effect is a general "jittery" feeling, but other side effects include restlessness, nervousness, gastrointestinal disturbances, muscle twitching, and in some extreme cases, cardiac arrhythmia.

A relaxant that is in widespread use today is kava. Kava, also known as kava-kava, yaquona, ava, ava-ava, awa, or kawa, is a member of the pepper family Piperceae. Kava is obtained from the rhizome and roots of *Piper methysticum Forst.* Kava is the most relaxing botanical herb with the exception of the opium poppy. Kava is known to induce general relaxation in humans when orally ingested, but it does not cause drowsiness or involuntary sleep. A liquid macerate of the kava root has been used on islands in the South Pacific in social gatherings and religious rituals for over three thousand years.

Recently, kava has been scientifically scrutinized and its psychoactive ingredients identified. These ingredients are referred to as kavalactones. A total of fifteen kavalactones have been identified to date, including kavain (a.k.a. kawain), dihydrokavain (a.k.a. dihydrokawain), methysticin, dihydromethysticin, yangonin, and demethoxy-yangonin. A synthetic version of kava, known as D,L-kavain is also available.

The specific kavalactones in kava root extract vary depending upon the origin of the kava plant. Further, the particular kavalactones present depend upon what part of the plant is used to prepare the extract. Kava roots, and their rhizomes, or distal root tips, are preferred, but other parts of the plant can be used. High quality extracts of kava are sold based upon the total kavalactone content, rather than upon analysis of the individual lactones contained therein.

Studies indicate that kavalactones can relieve nervous anxiety, tension, restlessness, as well as promote muscle relaxation. Studies have also shown that consumption of kavalactones does not impair neurophysiological activity, as evidenced by measurements of recognition rates, and driving ability. Further, kavalactones are non-addictive and do not induce involuntary sleep or symptoms of drunkenness. The German Commission E, a government-appointed panel that reviews herbal remedies, has approved kava to relieve anxiety and stress without side effects.

Traditionally, kava root is prepared for human consumption by pulverizing the root and/or rhizome and mixing it with water to obtain a liquid which can be consumed orally. Presently, kava root extracts are manufactured using ethanol as a solvent, as the kavalactones are readily soluble in ethanol. The extracted material is a yellowish brown paste or powder, which is tested to determine the weight percentage of kavalactones. Synthetic versions of kava are also available.

Today, kava is widely available as an herbal supplement in the form of pills, tablets and capsules made of pharmaceutical grade extract. For example, kava root extract is commercially available in single dose formulations containing from about 2% by weight to 30% by weight (i.e., 2% to 30% by wt) active kavalactones.

In view of the foregoing, it would be highly desirable to provide a dietary supplement having a stimulatory effect coupled with a general calming effect, thereby producing a synergistic combination that allows individuals or animals to remain awake and efficient, but also composed and relaxed. It would also be desirable to provide a diet aid or appetite suppressant that does not promote anxiety.

SUMMARY OF THE INVENTION

In accordance with the present invention, compositions are provided that comprise kavalactones and methylxanthines. The compositions of the present invention balance the energizing effects of methylxanthines with the calming effects of kavalactones. The compositions of the invention are used for promoting an alert state in a host subject without promoting anxiety. Additionally, the composition reduces appetite without promoting anxiety. The invention compositions can additionally contain other ingredients such as vitamins and minerals and may be provided in a variety of formulations.

DETAILED DESCRIPTION OF THE PREFERRED EMBODIMENTS

The compositions of the invention comprise kavalactones and methylxanthines in synergistic combinations that produce a wakeful, yet tranquil state. The composition also had the unforseen benefit of suppressing appetite. The stimulant employed in the compositions is a methylxanthine, or mixtures of methylxanthines. A preferred stimulant is caffeine (1,3,7-trimethylxanthine) which can be obtained from coffee beans, tea leaves, cola nuts, guarana, cacao seeds, or mate. Synthetic caffeine may also be utilized in the present invention. Additional methylxanthines that may be used in the present invention include 1,3-dimethylxanthine (present in tea) and 3,7-dimethylxanthine (present in cacao), as well as mixtures thereof.

Caffeine (1,3,7-trimethylxanthine) is available from well known sources such as coffee beans, tea leaves, cola nuts and cacao seeds. For example, the caffeine in chocolate, cocoa, and cocoa butter is obtained from cacao seeds. Less well known sources of caffeine are guarana and mate. Mate is made from a South American evergreen tree (*Ilex paraguariensis*) whose leaves contain caffeine. Mate is customarily consumed as a tea-like beverage. Guarana is a vine that climbs trees in South America, and grows as a shrub when cultivated in the open. The botanical name is *Paullinia cupana* H.B.K., variety *sorbilis*. Seeds cultivated from the plant yield guaranine, which has the same chemical composition as caffeine. A syrup extract is obtained from the seeds and used in soft drinks, or the seeds can be roasted and ground into powder.

The anti-anxiety, or relaxing components of the compositions of the invention are kavalactones, and include kavain (a.k.a kawain), dihydrokavain (a.k.a. dihydrokawain), methysticin, dihydromethysticin, yangonin, and demethoxyyangonin, among others. Kavalactones are obtained from the dried rhizome and roots of the kava plant. A pharmaceutical grade kava root extract, standardized to provide a kavalactone content of about 30% by wt and containing the full spectrum of lactones found in the kava plant may be employed in the compositions of the invention. However, lower or higher kavalactone contents (from 2% to 50% by wt) may also be used. A synthetic version of kava may also be utilized. This synthetic version comprises both the D and L forms. The individual kavalactones may be obtained commercially and utilized individually or combined to provide all of the kavalactones present in the native plant.

An unforseen beneficial use of the present invention is for appetite suppression. Obesity is a chronic condition that is prevalent in many societies. Obesity is an unhealthy condition and substances and treatments for weight reduction are widespread. Existing therapies for obesity can include establishing a negative energy balance. Generally, this is accomplished by ingestion of a sympathomimetic drug which stimulates thermogenesis, i.e., increases the metabolic rate. Known thermogenic drugs are ephedrine, phenylpropanolamine and caffeine. See, for example, Astrup, A. V., Treatment Of Obesity With Thermogenic Agents, Nutrition, 5, p. 70, 1989; Bray, Nutrition Reviews, 49, p. 33, 1991.

The present invention uses a composition of at least one kavalactone and at least one methylxanthine to increase the metabolic rate of the body. The therapeutically active ingredient kava has antidepressant properties and calming effects. An unexpected benefit of the composition comprising at least one kavalactone and at least one methylxanthine is that it also functions to reduce weight by acting as an appetite suppressant.

Additionally, it is well known that many people over-eat to satisfy feelings of anxiety. That is, people eat not for the purpose of satisfying hunger and meeting metabolic needs, but to satisfy secondary needs. It is hypothesized that the relaxing effect of kava reduces these secondary needs. Additionally, kava is known to cause a local anesthetic effect in the mouth, and a second hypothesis is that kava may cause similar effects in the stomach, thereby reducing appetite.

Compositions of the present invention may be formulated for administration to any suitable subject (human or animal) by any conventional route such as oral, rectal, or nasal. Thus the composition may be a tablet, capsule, suspension, emulsion, solution, suppository, or spray. The composition can be formulated to provide a homogenous mixture, or alternatively, the composition can be formulated so that the kavalactone component and the methylxanthine component are non-homogenous.

Formulations for oral use include tablets or capsules which contain the active ingredients mixed optionally with pharmaceutically acceptable inert excipients. Such excipients include for example: inert diluents such as calcium carbonate, sodium chloride, lactose, calcium phosphate, sodium phosphate, etc.; granulating and disintegrating agents, for example, potato starch, alginic acid, etc.; binding agents, for example, starch, gelatin or acacia, etc.; and lubricating agents for example, magnesium stearate, stearic acid or talc. Other pharmaceutically acceptable excipients include colorants, flavoring agents, plasticizers, humectants, etc. Tablets provided in accordance with the present invention may be uncoated or they may be coated by known techniques.

Alternatively, the active ingredients of the present invention may be delivered over an extended time period by delaying disintegration and absorption in the gastrointestinal tract to provide a sustained release effect. A time delay material such as glyceral monostearate or glycerol distearate may be employed for this purpose. Extended release formulations that may be employed to deliver the active ingredients of the invention are well known in the art. See, for example, Baker, Richard, Controlled Release Of Biologically Active Agents, John Wiley And Sons, 1986.

In certain embodiments, the active ingredient(s) may be delivered in a soft or hard gel capsule by mixing the active ingredient with water or an oil such as peanut oil or olive oil and enclosing the resulting formulation in a capsule.

The dosage may also be administered as an oral liquid dosage form by suspending the active ingredients or extracts thereof in an aqueous solution in admixture with a dispersing or wetting agent, suspending agent and one or more preservatives. Suitable dispersing or wetting agents are, for example, naturally occurring phosphatides, for example, lecithin, or condensation products of ethylene oxide, fatty acids, long chain aliphatic acids, or a partial ester derived from fatty acids and a hexitol or hexitol anhydrides, for example, polyoxyethylene stearate, polyoxyethylene sorbitol monooleate, polyoxyethylene sorbitan monooleate, etc. Suitable suspending agents are, for example, sodium carboxymethylcellulose, methylcellulose, sodium alginate, etc.

For rectal applications, suitable formulations for compositions according to the present invention include suppositories (emulsion or suspension type), and rectal gelatin capsules (solution or suspensions). In a typical suppository formulation, the active ingredients are combined with an appropriate pharmaceutically acceptable suppository base such as cocoa butter, esterified acids, glycerinated gelatin, and various water soluble or dispersible bases like polyethylene glycols and polyoxyethylene glycols and polyoxyethylene sorbitan fatty acid esters.

One embodiment of the invention comprises a composition containing about 50 to 350 mg kava root extract—containing about 2% to 50% by weight kavalactones—and about 50 to 250 mg caffeine—containing about 10% to 100% by weight 1,3,7-trimethylxanthine. In another embodiment, 1,3-dimethylxanthine or 3,7-dimethylxanthine can be substituted for 1,3,7-trimethylxanthine.

An alternative embodiment of the present dietary supplement comprises kava root extract and caffeine in about a one-to-one ratio of active ingredients. Other embodiments may vary the ratio of active ingredients from: one part kava to nine parts caffeine, to: nine parts kava to one part caffeine.

A preferred formulation would comprise about 100 mg kava root extract (containing about 30% by wt kavalactones), and 100 mg caffeine (containing anywhere from about 30% by wt to 100% by wt 1,3,7-trimethylxanthine) in a capsule or tablet with any necessary inert excipients. Another preferred embodiment would contain 200 mg kava root extract (with about 30% by wt kavalactones), and 200 mg caffeine (containing anywhere from about 30% by wt to 100% by wt 1,3,7-trimethylxanthine) in a capsule or tablet, with any necessary inert excipients. One embodiment administers the formula at intervals throughout the day every 2 to 5 hours as necessary.

Alternatively, the formulation may contain only one component, either kava, or caffeine in the above-described ranges, with both components packaged together, thus allowing more flexibility in individual dosages. For example, the present dietary supplement may comprise capsules or tablets containing 50 mg kava root extract (with about 30% by wt kavalactones) and capsules or tablets containing 50 mg caffeine (containing anywhere from about 30% by wt to 100% by wt 1,3,7-trimethylxanthine), packaged together so that the ratio of the two components can be varied to achieve the desired effect of an alert, yet calm state.

Other Embodiments

Throughout the above description, the preferred embodiment and other examples should be considered as exemplars, rather than as limitations on the present invention. While I have described the invention by means of specific embodiments, it is to be understood that numerous changes and modifications may be made therein without departing from the spirit and the scope of the invention as shown in the appended claims. Accordingly, it is appropriate that the appended claims be construed broadly and in a manner consistent with the spirit and scope of the invention herein described.

What is claimed is:

1. A diet aid comprising:
a composition of at least one kavalactone and at least one methylxanthine in a dosage effective to suppress the appetite.

2. The composition according to claim 1, wherein said kavalactone is obtained from *Piper methysticum*.

3. The composition according to claim 1, wherein the kavalactone is selected from the group consisting of kavain, kawain, dihydrokavain, dihydrokawain, methysticin, dihydromethysticin, yangonin, demethoxyyangonin and mixtures thereof.

4. The composition according to claim 1, wherein said kavalactone is obtained synthetically.

5. The composition according to claim 1, wherein said methylxanthine is selected from the group consisting of 1,3,7-trimethylxanthine, 1,3dimethylxanthine, 3,7-dimethylxanthine and mixtures thereof.

6. The composition according to claim 1, wherein said methylxanthine is obtained synthetically.

7. The composition according to claim 1, further comprising at least one substance selected from the group consisting of inert diluents, granulating and disintegrating agents, binding agents, lubricating agents, plasticizers, humectants, electrolytes, buffers, colorants, aromatic agents, flavoring agents, emulsifying agents, compounding agents, formulation agents, permeation enhancers and bulking agents.

8. The composition according to claim 1, wherein the ratio of kava to caffeine ranges from 1:10 to 10:1.

9. The composition according to claim 1, wherein the caffeine contains from about 10% to 100% by weight 1,3,7-trimethylxanthine.

10. The composition according to claim 1, wherein said kava is present as a root extract containing from about 2% to 50% by weight active kavalactones.

11. The composition according to claim 1 in a sustained release form.

12. A method for promoting appetite suppression in a host subject without promoting anxiety, the method comprising the steps of:
administering a composition of at least one kavalactone and at least one methylxanthine in a dosage effective to suppress the appetite.

13. The method according to claim 12, wherein the ratio of kava to caffeine ranges from 1:10 to 10:1.

14. The method according to claim 12, wherein the caffeine is obtained from at least one natural substance selected from the group consisting of coffee beans, tea leaves, cola nuts, guarana, cacao seeds and mate.

15. The method according to claim 12, wherein the caffeine is synthetically produced.

16. The method according to claim 12, wherein the caffeine contains from about 10% to 100% by weight 1,3,7-trimethylxanthine.

17. The method according to claim 12, wherein said kava is obtained from the *Piper methysticum* and comprises at least one kavalactone selected from the group consisting of kavain, kawain, dihydrokavain, dihydrokawain, methysticin, dihydromethysticin, yangonin, and demethoxyyangonin or mixtures thereof.

18. The method according to claim 12, wherein said kava is present as a root extract containing from about 2% to 50% by weight active kavalactones.

19. The method according to claim 12 in a sustained release form.

20. The method according to claim 12, further comprising at least one substance selected from the group consisting of inert diluents, granulating and disintegrating agents, binding agents, lubricating agents, plasticizers, humectants, electrolytes, buffers, colorants, aromatic agents, flavoring agents, emulsifying agents, compounding agents, formulation agents, permeation enhancers and bulking agents.

21. A method for obtaining weight reduction in a host subject, the method comprising the steps of taking a dosage of:
about 2% to 50% by weight kavalactones selected from the group consisting of kavain, kawain, dihydrokavain, dihydrokawain, methysticin, dihydromethysticin, yangonin, demethoxyyangonin and mixtures thereof; and
about 50% to 100% by weight methylxanthine selected from the group consisting of 1,3,7-trimethylxanthine, 1,3-dimethylxanthine and 3,7-dimethylxanthine.

22. The method according to claim 21, wherein said kavalactone is obtained from *Piper methysticum*.

23. The method according to claim 21, wherein said kavalactone is obtained synthetically.

24. The method according to claim 21, wherein said methylxanthine is obtained synthetically.

25. The method according to claim 21, further comprising at least one substance selected from the group consisting of inert diluents, granulating and disintegrating agents, binding agents, lubricating agents, plasticizers, humectants, electrolytes, buffers, colorants, aromatic agents, flavoring agents, emulsifying agents, compounding agents, formulation agents, permeation enhancers and agents.

26. The method according to claim 21, wherein the ratio of kava to caffeine ranges from 1:10 to 10:1.

27. The method according to claim 21 in a sustained release form.

* * * * *

UNITED STATES PATENT AND TRADEMARK OFFICE
CERTIFICATE OF CORRECTION

PATENT NO. : 6,025,363
DATED : February 15, 2000
INVENTOR(S) : James A. Giles, Jr.

It is certified that error appears in the above-identified patent and that said Letters Patent is hereby corrected as shown below:

Column 6,
Claim 8,
Starting Line 6, delete "wherein the ratio of kava to caffeine ranges from 1:10 to 10:1." and insert -- wherein a ratio of kavalactone to methylxanthine ranges from 1:10 to 10:1. --

Claim 9,
Line 9, delete "caffeine" and insert -- methylxanthine --.

Claim 10,
Starting line 11, delete "said kava" and insert -- the kavalactone --.

Claim 13,
Starting line 23, delete "the ratio of kava to caffeine ranges from 1:10 to 10:1." and insert -- wherein a ratio of kavalactone to methylxanthine ranges from 1:10 to 10:1. --

Claim 14,
Line 25, delete "caffeine" and insert -- methylxanthine --.

Claim 15,
Line 30, delete "caffeine" and insert -- methylxanthine --.

Claim 16,
Line 32, delete "caffeine" and insert -- methylxanthine --.

Claim 17,
Line 34, delete "said kava" and insert -- the kavalactone --.

Claim 18,
Line 41, delete "said kava" and insert -- the kavalactone --.

UNITED STATES PATENT AND TRADEMARK OFFICE
CERTIFICATE OF CORRECTION

PATENT NO.    : 6,025,363
DATED         : February 15, 2000
INVENTOR(S)   : James A. Giles, Jr.

It is certified that error appears in the above-identified patent and that said Letters Patent is hereby corrected as shown below:

Column 8,
Claim 26,
Starting line 3, delete "wherein the ratio of kava to caffeine ranges from 1:10 to 10:1." and insert -- wherein a ratio of kavalactone to methylxanthine ranges from 1:10 to 10:1. --

Signed and Sealed this

Twenty-fifth Day of September, 2001

Attest:

*Nicholas P. Godici*

NICHOLAS P. GODICI
*Attesting Officer*     *Acting Director of the United States Patent and Trademark Office*